United States Patent [19]

Boctor et al.

[11] Patent Number: 5,281,528

[45] Date of Patent: Jan. 25, 1994

[54] PROCESS FOR PURIFIED THROMBOPLASTIN FOR ULTRA-PURE THROMBIN PREPARATION

[75] Inventors: Amal Boctor, Long Valley; Surendra Mehta, Randolph; Galen Radebaugh, Chester, all of N.J.

[73] Assignee: Warner-Lambert Company, Morris Plains, N.J.

[21] Appl. No.: 973,014

[22] Filed: Nov. 6, 1992

Related U.S. Application Data

[60] Division of Ser. No. 657,427, Feb. 22, 1991, which is a continuation-in-part of Ser. No. 452,174, Dec. 18, 1989, abandoned.

[51] Int. Cl.$^5$ ............................................. C12N 9/48
[52] U.S. Cl. ........................................ 435/212; 435/814; 435/815
[58] Field of Search ....................... 435/212, 814, 815

[56] References Cited

U.S. PATENT DOCUMENTS

| | | | |
|---|---|---|---|
| 2,408,535 | 10/1946 | Smith | 435/212 |
| 2,541,676 | 2/1951 | Studer et al. | 435/212 |
| 2,687,980 | 8/1954 | Blanchard et al. | 435/212 |
| 2,842,480 | 7/1958 | Singher et al. | 435/212 |
| 2,847,350 | 8/1958 | Singher et al. | 435/212 |
| 3,983,004 | 9/1976 | Trobisch et al. | 435/212 |
| 4,416,812 | 11/1983 | Becker et al. | 435/212 |
| 5,017,556 | 5/1991 | O'Brien et al. | 514/2 |

FOREIGN PATENT DOCUMENTS

| | | |
|---|---|---|
| 0221700 | 5/1987 | European Pat. Off. . |
| 0378798 | 7/1990 | European Pat. Off. . |
| 0439156 | 7/1991 | European Pat. Off. . |
| 0212449 | 2/1968 | U.S.S.R. ........... 435/212 |
| 9005740 | 5/1990 | World Int. Prop. O. . |

OTHER PUBLICATIONS

Bjorklid et al. (1973) *Biochem. Biophys. Res. Comm.*, 55(3) 969–976.
Bach et al. (1987) *J. Biol. Chem.*; 256(16), 8324–8331.
Guha et al., (1986) *Proc. Nat. Acad. Sci., USA*, 83, 299–302.
Freyssinet et al. (1986) *Thromb, Haemostasis*, 55(1), 112–118.
Liu et al. (1975) *Thromb. Res.*, 7(1), 199–211.
Wijngaards et al. (1977) *Haemostasis*, 6(5), 269–282.
Bayer et al. (1975) *Acta Haematol.*, 54(3), 165–171.

*Primary Examiner*—Douglas W. Robinson
*Assistant Examiner*—Jon P. Weber
*Attorney, Agent, or Firm*—Ronald A. Daignault; Elizabeth M. Anderson

[57] ABSTRACT

A process for the manufacture of purified thromboplastin used in the manufacture of an ultra-pure, clear thrombin solution is described.

3 Claims, 1 Drawing Sheet

PROCESS FOR PURIFIED THROMBOPLASTIN FOR ULTRA-PURE THROMBIN PREPARATION

CROSS REFERENCE TO RELATED APPLICATIONS

This is a divisional of U.S. application Ser. No. 657,427 filed Feb. 22, 1991, now pending, which is a continuation-in-part of U.S. application Ser. No. 452,174 filed Dec. 18, 1989, now abandoned.

BACKGROUND

Thrombin, a proteolytic enzyme, is essential for hemostasis. It is a principle reagent in the formation of blood clots via fibrin production. Due to its effectiveness as a clotting aid, thrombin and its preparations are useful during surgical procedures to control bleeding. While dry thrombin is available, liquid preparations are generally preferred due to handling and time considerations.

Until now, there have been no highly stable, clear liquid thrombin preparations which are both storage stable and ready for use during surgery. This is because thrombin, when dissolved in water or saline, rapidly loses its activity due to denaturation and autolysis of the thrombin protein.

THE INVENTION

The present invention is directed to a novel modification of a process for the preparation of thrombin of ultra-pure quality in solution. This solution is completely clear and free of turbidity, and has a characteristic of high clotting activity, less inactive protein, and a high specific activity, more than any thrombin product hereto described.

The novelty of the present process, which achieves the goal of a clear thrombin solution, is the unique combination of a whole host of steps in a particular sequence.

First of all, the common thrombin, in circulating blood, exists in an inactive form called prothrombin and a factor called thromboplastin is required in order to convert prothrombin to thrombin. The present invention does not involve the usual use of bovine lung extract as a source of thromboplastin but uses an isolated, highly purified thromboplastin, as described hereinafter. This process eliminates a significant amount of contaminating proteins which are the probable source of impurities and turbidity often seen in a final product.

The prothrombin to thrombin conversion mixture, following the usual centrifugation step, is passed through an anion exchange chromatography column, affording an eluted material which is still turbid. This material is then, in the present invention, frozen and then thawed, followed by centrifugation to remove most of the turbidity. Removal of this turbidity improves the solution flow through the second stage cation-exchange column chromatography procedure.

Following the second passage of the solution through a cation exchanger, the improvement in this step comprises eluting the material through this column by a normal flow from top to bottom with a salt gradient rather than a standard sodium chloride solution.

The results of these modifications have provided the isolation of a water-clear, ultra-pure thrombin, the specific activity being much superior to any product available on the market, as shown in Table 1.

TABLE 1

Comparison Between Thrombostat ®, Thrombinar ®, and Ultra-Pure Thrombin

|  | Thrombostat ®[a] | Thrombinar ®[b] | Ultra-Pure |
|---|---|---|---|
| Clotting activity[c] (U/mL) | 2164 | 1372 | 7820 |
| Protein (mg/mL) | 11.56 | 0.82 | 0.82 |
| Specific activity (U/mg) | 187 | 1663 | 9500 |

[a]Parke-Davis
[b]Armour
[c]Determined by a modified NIH method hereinafter described.

Accordingly, the present invention concerns, in its broadest aspects:

I. An ultra-pure, clear, colorless thrombin solution having specific activity from 4000 to 11,000 Units/mg protein.

II. An ultra-pure, clear, colorless thrombin solution prepared by reacting prothrombin with purified thromboplastin and treating the resulting thrombin, after centrifugation, by eluting the supernatant through an anion-exchange agarose column; freezing, then thawing up to about 25° C., the desired eluant fractions; centrifuging and eluting the supernatant through a cation-exchange agarose column with a salt gradient in a buffer.

III. A process for preparing an ultra-pure, clear, colorless thrombin solution comprising:

reacting prothrombin with purified thromboplastin; centrifuging the suspension; eluting the supernatant through an anion-exchange agarose column with buffer; freezing then thawing up to about 25° C. the desired eluant fractions; centrifuging and eluting the supernatant through a cation-exchange agarose column with a salt gradient in a buffer.

ADVANTAGES

The thrombin compositions and methods of the invention have several advantages over conventional preparations and methods for assisting in blood clotting.

Unlike powdered preparations, the compositions of the instant invention require no reconstitution prior to use. Thus, measuring, mixing, sterilizing, etc. of one or more component(s) or container(s) are not important considerations. The instant clear preparations can be used without preparation before final use because of the absence of particles which cause the turbidity in former liquid preparations.

Furthermore, the stability of the instant thrombin-containing materials is such that the need for stock inventories and/or rotation of products is largely eliminated. Unlike most saline or water-solutions of thrombin, which are stable for only about one week at 4° C., the instant preparations are designed to be stable at normal refrigeration temperatures (i.e., about 4° C.) and at room temperature (i.e., about 25° C.) for 6 months or more.

It is known that high concentrations of glycerol, sucrose, and other polyols can stabilize proteins in solution. In the case of thrombin, it is known that a glycerol concentration of 67% can greatly stabilize a 1,000 μ/mL thrombin solution. However, use of high glycerol concentrations is not practical in the large scale manufacture of a sterile thrombin solution because of the high viscosity of such a preparation. The instant compositions, which may contain 30% or less, of glycerol avoid these problems.

Other advantages and aspects of the invention will become apparent from a consideration of the following description of the invention.

DETAILED DESCRIPTION OF THE PREFERRED EMBODIMENTS

Isolation of Thromboplastin From Lung Tissue

Figure 1:
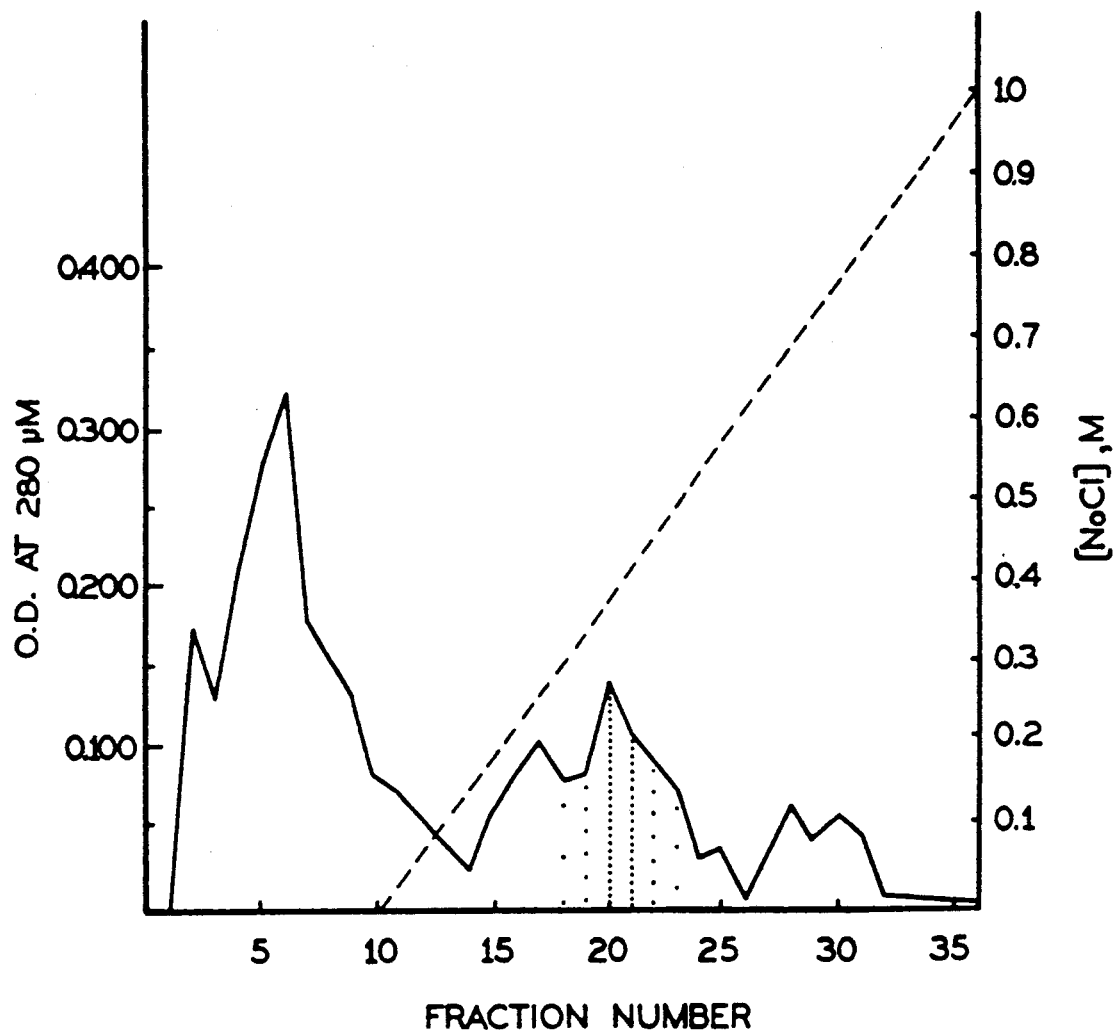
FIG. 1 is a graph showing the purification of thrombin by way of the profile of elution of the CM-Sepharose column using the salt gradient of 0.1 to 1.0M sodium chloride solution as described in the example.

Bovine/veal lung tissue is trimmed to remove fatty tissue, cut into small pieces, and homogenized in a tissue homogenizer with 25-50 mM phosphate buffer pH 6.2-6.7, preferably pH 6.5 containing 0.5-1.0% polysorbate 80. The surfactant aids in the extraction of the enzyme. Other nonionic surfactants can be used, e.g., fatty acid esters of polyoxyethylene sorbitan, e.g., Tween ®, ICI; polyoxyalkylyne fatty acid esters, e.g., MYRJ ®, ICI; polyoxyethylene fatty ethers, e.g., Brij ®, ICI; polyoxypropylene-polyethylene ethers, e.g., Pluronic ®, BASF; sucrose mono esters; and Triton X-100. The homogenate is centrifuged at 12-14K RPM and the supernatant is collected. The pH of the supernatant is adjusted to pH 5.2-5.7, preferably pH 5.5 using drops of 10% acetic acid and centrifuged at 12-14K RPM. The supernatant from this step is loaded on a conventional cation exchange crosslinked agarose column, e.g., CM-Sepharose ® (other cationic resins can be used, e.g., CM-Sephadex ®) and eluted with 25-50 mM phosphate buffer as described above. The eluate is monitored at 280 nM. The activity of thromboplastin in the eluate is also monitored indirectly by first converting prothrombin to thrombin and the latter activity is then determined by measuring clotting activity using a fibrometer.

The initial fractions eluting from the column form part of the first peak which contains thromboplastin. Fractions eluting later which are part of the second peak contain nonactive extraneous proteins. This purified thromboplastin solution is opalescent without any haze or turbidity. This fraction can be clarified further by a freeze/thaw and centrifugation cycle without any loss of prothrombin converting activity.

Preparation, Isolation, and Purification of Ultra-Pure Thrombin

Assay for Thrombin Activity

Thrombin clotting activity was determined using a modified NIH method. The solutions used consisted of: a) Imidazole buffer, stock, (IBS) made by dissolving 1.72 g imidazole in 90 mL of 0.1N hydrochloric acid and then made to 100 mL with distilled water (final pH should be about 7.2). b) PEG/IBS solution made by diluting IBS, 58.8 mL; sodium chloride, 9.0 g; and polyethylene glycol (PEG, molecular weight 8000), 5 g to 1000 mL with water. Normal human plasma was used as a source of fibrinogen and was diluted with 0.154M sodium chloride (1:1) prior to use. NIH thrombin was used as a standard and was diluted with polyethylene glycol (8000)/imidazole buffered saline (PEG/IBS) to give 5 U/mL. Clotting assay was performed using a fibrometer. Diluted plasma (200 μL) was incubated at 37° C. for 3 minutes, then standard thrombin (100 μL) was added and the clotting time (in seconds) was recorded (14 to 15 seconds). Thrombin-containing unknown sample was diluted with PEG/IBS to give clotting time values higher and lower than the standard clotting time value by about 5 seconds. Enzyme activity was calculated as follows:

$$\frac{\{[(A - B)(C - D)] + B\}g}{(E - D)} = \text{units/mL}$$

A: high dilution factor of unknown thrombin sample
B: low dilution factor of unknown thrombin sample
C: average clotting time of standard thrombin
D: average clotting time of low dilution of unknown thrombin sample
E: average clotting time of high dilution of unknown thrombin sample
g: units of standard thrombin in test mixture divided by volume of standard thrombin in test mixture (0.5/0.1)

Enzyme activity is expressed as Units/mL (up to 8000 U/mL) and as Units/mg protein (up to 10,000 U/mg protein).

Purified or partially purified bovine plasma prothrombin is reacted with purified thromboplastin in the presence of 10-40 mM calcium chloride solution at a temperature between 10° and 25° C. for 15-45 minutes as described under Example B, "Isolation of Ultra-Pure Thrombin". The amount of thromboplastin activity is two to three times that of prothrombin at pH 6.5-7.0. The thrombin produced by this reaction is further purified as follows. The resulting protein suspension is centrifuged (12K RPM) in a refrigerated centrifuge (2°-10° C.) to separate insoluble nonactive proteins. The supernatant is loaded on a weak anion-exchange column (DEAE-Sepharose ®, DEAE-Sephadex ®, DE-52 ®). The column is eluted with 20-50 mM phosphate buffer (pH 6.5) containing 0.1M sodium chloride (2°-10° C.). The eluant is monitored at 280 nM. Fractions with high UV absorbance are further checked for thrombin clotting activity (using a fibrometer). These pooled fractions containing thrombin are turbid and are clarified by freezing the suspension overnight, followed by thawing (<25° C.) and centrifugation or filtration. The thrombin-containing pool is loaded on a cation-exchange column (CM-Sepharose ®, CM-Sephadex ®) and eluted using a salt gradient (0.1M to 1M sodium chloride in 25-50 mM phosphate buffer, pH 6.5).

The eluant is monitored at 280 nM and the fractions containing thrombin activity (as determined by the fibrometer) are pooled (FIG. 1). The fractions containing ultra-pure thrombin are water clear and may have about 8000 U/mL of activity. The purity of ultra-pure thrombin is determined by reversed-phase HPLC, polyacrylamide gel electrophoresis, and isoelectric focusing.

Protein content of the thrombin fraction was determined using the Bradford assay (Bradford, M., Anal. Biochem., 72:248, 1976) and the protein reagent made by BioRad (Richmond, Calif.). Specific activity of the preparation was calculated by dividing the amount of enzyme units per unit volume into the amount of proteins per same unit volume.

The exceptionally high specific activity of thrombin made by the present invention is attributed to the following:

1. The use of a freshly harvested prothrombin yields a thrombin product of high specific activity. Also, inactive thrombin can co-elute with active thrombin and this can result in decreased specific activity of the final product. Therefore, all the isolation steps need to be carried out at a temperature between about 2° to 7° C. Furthermore, solutions were not allowed to stand, even refrigerated, for extended periods of time prior to use. Freezing at about −10° to −20° C. was adequate to protect the products.

2. The use of highly purified thromboplastin as described in the present invention diminishes the extent of contaminants or the presence of nonspecific proteins in the final thrombin preparation, hence increasing the specific activity.

The Thrombin Preparations

The preparations made in accordance with the invention must contain, in a liquid medium, ultra-pure thrombin, and one or more buffers. They may contain saline, and other substances conventionally employed in protein preparations.

While the term "preparations" is employed, it should be noted that Applicants contemplate all types of formulations in which thrombin, in substantially solubilized form, is present in combination with one or more glycols and buffers.

When a liquid formulation is made, it is generally preferred that the solvent(s) or other diluent(s) employed have a suitable miscibility with thrombin such that production standards, e.g., uniformity of thrombin concentration from batch to batch, can be readily met.

The thrombin employed is an ultra-pure thrombin obtained by the process of the present invention.

This thrombin solution is, if desired, then mixed with glycerol containing either acetate buffer or phosphate buffer and saline, in order to prepare a stabilized solution.

Thrombin is known to be soluble in physiological saline—i.e., a solution containing about 0.9% NaCl in water. However, other saline solutions are contemplated as useful herein. Furthermore, the replacement of all or part of the NaCl in such solutions with one or more other suitable salts is contemplated.

Water is a preferred medium for the preparations of the invention. However, the use of one or more other diluents which do not adversely affect the solubility and/or stability of thrombin in the subject preparations is desirable.

One such diluent is glycerol. Other useful polyols include mannitol, sorbitol, sucrose, glucose, and the like. Mixtures are operable. Glycerol is highly preferred.

The glycerol or other polyol ingredient(s) will be employed at a total concentration of from about 10 to about 40 wt. %, preferably 20 to 30 wt. % based on total composition weight.

Unless stated otherwise, all quantities recited are weight percentages based on total compositions weight.

Suitable buffer systems are those whose aqueous solutions will maintain pH of the final thrombin solution between about 5.0 and about 8.0, with a preferred pH range of about 5.5 to about 6.5. It is highly preferred that when a phosphate buffer is used the final pH of the preparation be about 6.0 to about 6.5 and when an acetate buffer is used, the final pH be about 5.0.

pH measurements are made using an ordinary pH meter with a combination electrode.

Useful buffer systems include acetate, phosphate, succinate, bicarbonate, imidazole, TRIS, and the zwitterionic buffers described by N. E. Good and S. Izawa, in *Methods in Enzymol*, 24, Part B, 53 (1972); and W. F. Ferguson, K. I. Braunschweiger, W. R. Braunschweiger, J. R. Smith, J. McCormick, C. C. Wasmann, N. P. Jarvis, D. H. Bell, and N. E. Good in *Anal. Biochem* 104, 300 (1980). These disclosures are hereby incorporated by reference.

Suitable reagents for use in the instant buffer systems include MES, ACES, BES, MOPS, TES, HEPES, and the like. Phosphate should only be used when calcium ion is absent or in the presence of EDTA. Mixtures of such reagents can be employed. If mixed buffers are used, the final pH should be suitably adjusted.

Buffers containing phosphate ion and acetate ions are preferred. Mixtures are operable.

The buffers will be present in the buffer solution, along with water and/or other suitable diluent(s) at total concentrations of about 0.01M to about 0.2M, preferably about 0.025M to about 0.10M.

The use of various other conventional additives, e.g., antioxidants, colorants, surfactants, and the like, is also contemplated. Glutathione may be employed as an optional ingredient. Amino acids may be employed as an optional ingredients, but their presence must not be in such quantities as to interfere with the stabilizing action of the polyol and buffer components on the purified thrombin. In general, it is preferred that they be used in only minute quantities at concentrations of 0.5% or less, if at all.

Hemostats

Hemostatic materials, such as GELFOAM ®, SURGICEL ®, and AVICEL ®, and collagen, which are presently used alone or in combination with thrombin powder or thrombin in saline, can be effectively used with the stabilized thrombin formulations of the present invention using a variety of techniques. Preferably, the stabilized solution is absorbed onto the hemostatic agent and the pad is freeze-dried and packaged in a sterile manner.

Antimicrobial or antibiotic agents can also be incorporated into such pads, especially for use on burn patients, where prevention of infection is critical.

One type of bandage suitable in the preparation of coagulants in accordance with the invention is set forth in U.S. Pat. No. 4,363,319, the disclosure of which is hereby incorporated by reference.

The following is illustrative of the preparation of an ultra-pure thrombin solution.

EXAMPLE

A. Isolation of Thromboplastin 100 g Veal lung was homogenized in 200 mL, 25 mM sodium phosphate buffer, pH 6.5, containing 0.5% polysorbate 80 and centrifuged at 12K RPM for 20 minutes at 5° C. The supernatant was collected and the pH adjusted to 5.72 using 10% acetic acid, and let stand in the refrigerator for 1 hour. The mixture was centrifuged for 20 minutes as above and the supernatant collected. 160 mL of the supernatant was loaded on a CM-Sepharose ® column (30×20.5 cm), which was saturated with 25 mM sodium phosphate buffer, pH 6.5, and eluted using the same buffer. Fractions of 230 drops were collected (about 13 mL) and the optical density at 280 nM of the fractions was measured.

| Tube No. | | OD at 280 nM |
|---|---|---|
| 1 | clear | 0.0 |
| 2 | clear | 0.0 |
| 3 | clear | 0.0 |
| 4 | opalescent | 1.369 |
| 5 | opalescent | 3.751 |
| 6 | opalescent | 3.828 |
| 7 | opalescent | 0.451 |
| 8 | yellowish | 3.427 |
| 9 | yellowish | 3.993 |
| 10 | reddish | 3.513 |
| 11 | reddish | 4.060 |
| 12 | reddish | 4.071 |
| 13 | reddish | 4.055 |
| 14 | reddish | 4.073 |
| 15 | reddish | 3.944 |
| 16 | reddish | 3.723 |
| Pool 1 fractions 4–6 | | |
| Pool 2 fractions 7–9 | | |

The pools were assayed for thromboplastin activity by converting prothrombin to thrombin as follows:

| Mix | prothrombin | 1.0 mL |
|---|---|---|
| | saline | 0.5 mL |
| | pool fract. | 0.1 mL |
| | CaCl₂ (0.3M) | 100 μL | incubated the mixture at 25° C. for 25 minutes, centrifuged at 5° C. at 13K for 10 minutes and assayed for thrombin clotting activity using a fibrometer.

| Fraction | Clotting time (seconds) |
|---|---|
| Pool 1 | 10.9 |
| Pool 2 | 9.9 |

The two pools contained significant thromboplastin (prothrombin converting) activity. The first pool was used for the conversion of prothrombin to thrombin since it has less color. The second pool, however, could be utilized also.

B. Isolation of Ultra-Pure Thrombin

| The conversion mix was made of: | |
|---|---|
| Prothrombin | 97 mL |
| saline | 40 mL |
| CaCl₂ (0.3M) | 10 mL |
| Thromboplastin (Pool 1) | 15 mL | incubated at 25° C. for 30 minutes and centrifuged at 13K for 20 minutes at 5° C., and collected the supernatant.

C. DEAE-Sepharose Column Chromatography

Equilibrated the column (30×2.5 cm) with 25 mM sodium phosphate buffer pH 6.5 containing 0.02% sodium azide. Sodium azide was used as a bacteriostatic agent, however, this agent cannot be used during the isolation of thromboplastin since it causes browning of the red hemoglobin. Other common bacteriostatic agents can be substituted and are preferred. These include phenols and substituted phenols, chlorobutobenzyl alcohol, benzalkonium chloride, benzethonium chloride, thimerosal, and phenylmercuric nitrate.

Loaded 115 mL of the converted preparation on the column and eluted using the same buffer containing 0.1M sodium chloride. Collected fractions of 230 drops and assayed for thrombin clotting activity.

Fractions 7–48 showed significant thrombin clotting activity; they were pooled (510 mL) and the material appeared turbid. The pooled material was kept in a plastic bag and frozen overnight. The material was thawed, centrifuged at 13K for 20 minutes at 5° C. and the supernatant collected.

D. CM-Sepharose Column Chromatography

Equilibrated the column (30×2.5 cm) with 25 mM sodium phosphate buffer, pH 6.5 containing 0.02% sodium azide and 0.1M sodium chloride.

Loaded 493 mL of the previous supernatant from the DEAE-sepharose column step.

Eluted the column with a salt gradient made of 225 mL of the buffer containing 0.02% sodium azide and 0.1M sodium chloride and 225 mL buffer containing 0.02% sodium azide and 1.0M sodium chloride. Fractions were collected as described above and assayed for thrombin clotting activity using a fibrometer.

Fractions 15–21 contained significant activity and were pooled (volume of 90 mL). The pooled material was then assayed for thrombin activity and showed clotting activity of 8213 U/mL.

This pooled fraction was also assayed for protein content using the Bradford method and Bio-Rad protein assay kit. The pooled material contained 0.82 mg/mL protein.

Final specific activity = 8213/0.82 = 10015 U/mg protein.

We claim:

1. A process for the preparation of purified thromboplastin which comprises
   (a) homogenizing bovine lung tissue with 25 mM phosphate buffer, pH 6.5, containing about 0.5 to about 1.0% of a nonionic surfactant; and centrifuging the mixture;
   (b) adjusting the pH of the supernatant to 5.5 with 10% acetic acid and centrifuging;
   (c) eluting the supernatant through a carboxymethylcellulose column with 25–50 mM phosphate buffer; and collecting the desired fractions.

2. The process of claim 1, wherein the desired fractions are further clarified by freezing then thawing up to about 25°; centrifuging, and collecting the supernatant.

3. The process of claim 1 wherein veal lung tissue is homogenized in step (a).

* * * * *